US007544948B2

(12) United States Patent
Schönlein et al.

(10) Patent No.: US 7,544,948 B2
(45) Date of Patent: Jun. 9, 2009

(54) CONTROL OF THE UV RADIATION SOURCES FOR A WEATHERING APPARATUS ON THE BASIS OF THE AVERAGED RADIATION INTENSITY

(75) Inventors: Artur Schönlein, Rüsselsheim (DE); Bernhard Börner, Freigericht (DE); Bernd Rudolph, Alzenau (DE); Peter March, Frankfurt (DE)

(73) Assignee: Atlas Material Testing Technology GmbH (DE)

( * ) Notice: Subject to any disclaimer, the term of this patent is extended or adjusted under 35 U.S.C. 154(b) by 165 days.

(21) Appl. No.: 11/195,846

(22) Filed: Aug. 3, 2005

(65) Prior Publication Data

US 2006/0049360 A1 Mar. 9, 2006

(30) Foreign Application Priority Data

Aug. 3, 2004 (DE) ................ 10 2004 037 603

(51) Int. Cl.
*G01J 1/42* (2006.01)
(52) U.S. Cl. .................................... 250/372
(58) Field of Classification Search ........... 250/372, 250/252.1, 504 R, 492.1, 493.1, 395, 505.1, 250/494.1
See application file for complete search history.

(56) References Cited

U.S. PATENT DOCUMENTS

| 4,665,627 | A | | 5/1987 | Wilde et al. |
| 4,985,622 | A | * | 1/1991 | Kessler et al. ............... 250/226 |
| 5,206,518 | A | * | 4/1993 | Fedor et al. ............. 250/504 R |
| 5,220,840 | A | | 6/1993 | Neigoff et al. |
| 5,374,825 | A | * | 12/1994 | Doty et al. ................... 250/372 |
| 6,264,836 | B1 | * | 7/2001 | Lantis ......................... 210/188 |
| 6,517,687 | B1 | * | 2/2003 | Iacovangelo ........... 204/192.26 |
| 6,946,652 | B2 | * | 9/2005 | Rathod et al. ............. 250/252.1 |
| 7,013,742 | B2 | * | 3/2006 | Beraud ....................... 73/865.6 |
| 7,118,271 | B2 | * | 10/2006 | Schonlein et al. ............... 374/2 |
| 2001/0038269 | A1 | * | 11/2001 | Grossman et al. ........... 315/291 |
| 2002/0062787 | A1 | | 5/2002 | Hashizume et al. |
| 2002/0139928 | A1 | * | 10/2002 | Rathod et al. ............. 250/252.1 |
| 2005/0205769 | A1 | * | 9/2005 | Ishikawa et al. ............ 250/234 |
| 2008/0210884 | A1 | * | 9/2008 | Egberts ....................... 250/429 |

FOREIGN PATENT DOCUMENTS

| DE | 2043217 A1 | 9/1970 |
| DE | 2940325 A1 | 10/1979 |
| EP | 1571439 A2 | 9/2005 |

* cited by examiner

*Primary Examiner*—David P Porta
*Assistant Examiner*—Faye Boosalis
(74) *Attorney, Agent, or Firm*—Vedder Price P.C.

(57) ABSTRACT

The radiation power emitted from the UV radiation sources (2) in a weathering apparatus is controlled such that the radiation power of each of the radiation sources (2) is measured in a predetermined spectral range of the radiation emitted from the radiation sources, with the spectral range being chosen such that the measured radiation power is representative of the radiation power in the UV, an averaged radiation power is calculated from the measured radiation powers, and the averaged radiation power is used for controlling the electrical power to be supplied to the radiation sources (2). In particular, the control process can be carried out in such a way that the same electrical power, within a predetermined tolerance bandwidth, is supplied to each of the radiation sources (2), and the averaged radiation power is kept constant over time at a desired nominal value.

10 Claims, 1 Drawing Sheet

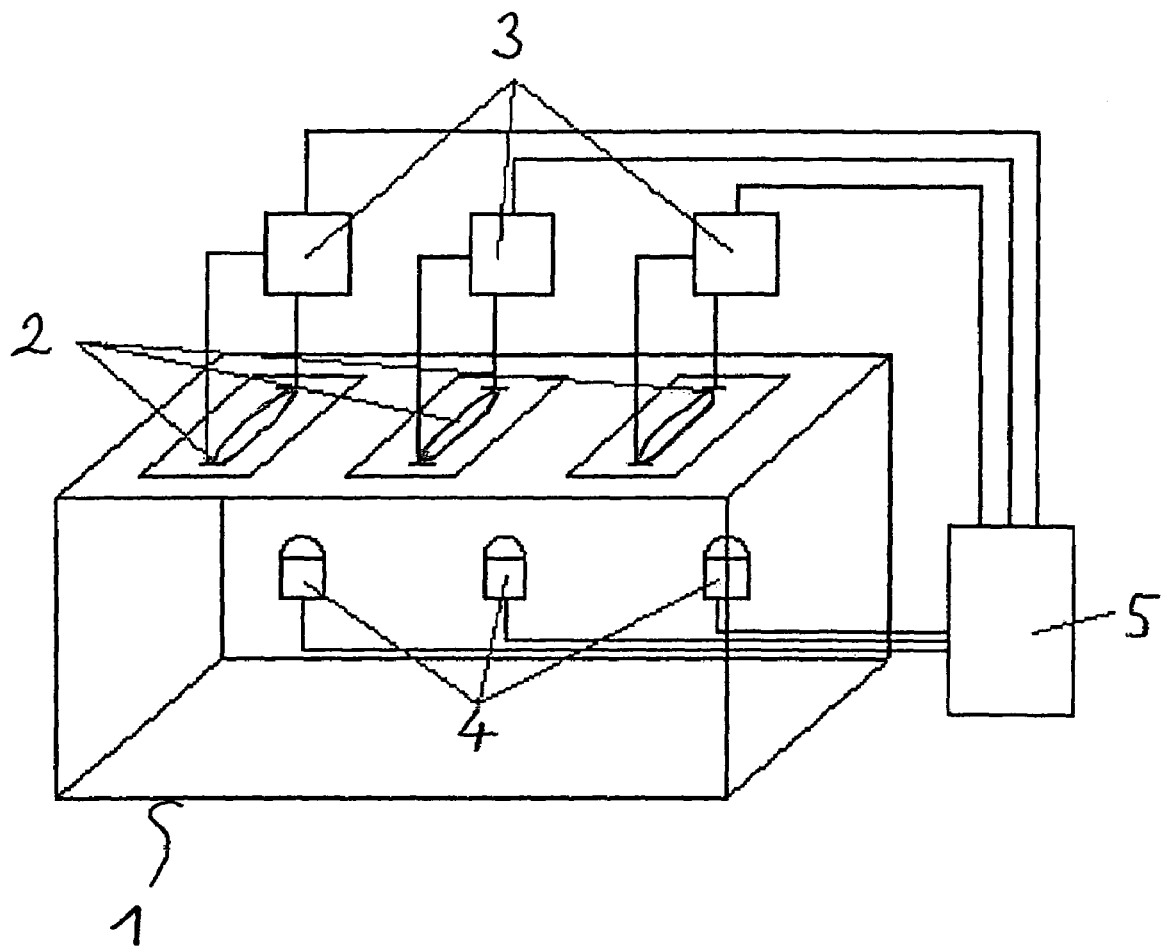

CONTROL OF THE UV RADIATION SOURCES FOR A WEATHERING APPARATUS ON THE BASIS OF THE AVERAGED RADIATION INTENSITY

FIELD OF THE DISCLOSURE

The present invention relates to a method and an arrangement for controlling the UV radiation sources in a weathering apparatus.

BACKGROUND

In a weathering apparatus, the weather-dependent ageing behaviour of a sample, in particular of a flat material sample, is assessed, with the sample being subjected to artificial weathering. The weathering apparatus for this purpose normally has a weathering chamber, in which holding means are arranged for holding samples to be weathered, and in which one or more radiation sources are arranged in order to apply radiation, in particular UV radiation, to the samples.

SUMMARY

Apparatuses for artificial weathering of material samples are generally used to estimate the life of materials which are continuously subjected to natural weather conditions during their use, and which thus deteriorate under climatic influences such as sunlight, solar heat, humidity and the like. In order to obtain a good simulation of the natural weathering characteristics, it is advantageous for the spectral energy distribution of the light produced in the apparatus to correspond as far as possible to that of the natural solar radiation, for which reason appliances such as these use xenon emitters as their radiation source. An accelerated ageing test of the materials is achieved essentially by illuminating the samples much more intensively than the natural conditions, thus speeding up the ageing of the samples. A statement about the long-term ageing behaviour of a material sample can thus be made after a relatively short time.

The majority of the material samples which are investigated in artificial weathering appliances are composed of polymer materials. The weather-dependent deterioration of polymer materials is caused substantially by the UV component of the solar radiation. The primary photochemical processes which take place in this case, that is to say the absorption of photons and the production of stimulated states or free radicals, are not dependent on the temperature. In contrast, the subsequent reaction steps with the polymers or additives may be dependent on the temperature, so that the observed ageing of the materials is likewise dependent on the temperature.

The already known weathering apparatuses normally use a number of UV radiation sources such as xenon radiation sources. As is known, these can be used to simulate the solar spectrum quite well, but the emitted radiation has a relatively high spectral component in the infrared spectral range. Within the life of a commercially available xenon radiation source of about 1500 hours, the emitted UV radiation power, relative to the electrical power that is supplied, decreases continuously. In order nevertheless to keep the UV radiation power constant over the entire life, in particular within a weathering process, however, a control system is used in conventional weathering apparatuses. This provides for the radiation power emitted from each UV radiation source to be measured individually by means of a UV sensor, and for its output signal to be used as a controlled variable for the electrical power to be supplied to the UV radiation source. Each of the control loops reacts to a reduction in the radiation power by increasing the electrical power that is supplied, so as to achieve the original radiation power again.

This individual control of the radiation sources has the advantage that the UV radiation power of all of the radiation sources can be kept constant at one and the same level over time. However, the disadvantage is that the normally used radiation sources, in particular xenon radiation sources, do not degrade in the infrared range, or do not degrade as severely as in the UV range. The application of a different electrical power to the radiation sources in order to compensate for the differences in the UV radiation power thus leads to the radiation sources emitting different radiation powers in the infrared. However, this means that the samples to be weathered are heated to different extents, and different temperatures occur on them. The results of the weathering process are thus reliable only to a limited extent owing to the ageing temperature dependencies mentioned above.

A further disadvantage of applying different electrical powers to the radiation sources is that the radiation sources which are loaded to a greater extent age more quickly because they are more highly loaded, so that even more electrical power must be applied to them in a self-reinforcing process, owing to the faster ageing. This can lead to a considerable shortening of their lives.

One object of the present invention is therefore to specify a method and an arrangement for controlling the radiation sources in a weathering apparatus, which provide satisfactory control of the radiation sources without temperature imbalances being produced on the samples and/or without excessively shortening the life of the radiation sources. One particular aim is to counteract the processes of the UV radiation powers of the radiation sources drifting apart, without this leading to differences in the infrared radiation power.

This object is achieved by the features of the independent patent claims. Advantageous developments and refinements are specified in the dependent claims.

One major aspect of the invention is to determine the mean radiation power of the UV radiation sources in the weathering apparatus and to use this for control purposes. The radiation sources are thus no longer controlled individually, but their radiation powers are detected and are averaged, and the radiation sources are controlled on the basis of the averaged radiation power.

Thus, in the method according to the invention, the radiation power of each of the radiation sources is measured in a predetermined spectral range of the radiation emitted from the radiation sources, with the spectral range being chosen such that the measured radiation power is representative of the radiation power in the UV. An averaged radiation power is then calculated from the measured radiation powers, and the averaged radiation power is used for controlling the electrical power to be supplied to the radiation sources.

The radiation power of the radiation sources is preferably measured directly in the UV range. This can advantageously be achieved by using UV broadband sensors with a sensitivity range from 300 nm to 400 nm. Sensors for a spectrally narrower sensitivity range, for example 330-350 nm, may however also be chosen. Since the radiation source can be designed such that it emits not only in the UV but at least in one sub-band of the adjacent visible spectral range as well, the radiation power can also be measured outside the UV, for example in the visible blue spectral range by means of a sensor with a sensitivity range from 410 nm to 430 nm. This is dependent on the spectral measurement range being chosen such that the measured radiation power is representative of the radiation power in the UV, in particular of the radiation power integrated over the entire UV range. In particular, a fixed ratio may exist between two radiation powers, such that the radiation power in the UV can be calculated at all times by multiplication of the radiation power in the visible by a constant.

The concept according to the invention thus includes a control process in which the decrease in the UV radiation power of an individual radiation source is compensated for not just by this on its own and, instead, the compensation power to be applied is distributed uniformly between all of the radiation sources. There is no longer any need for each individual radiation source to supply a constant UV radiation power. In fact, the critical factor is that the mean UV radiation power behaves as specified, in particular by remaining constant over time.

In consequence, fundamentally, there is now only one common control loop rather than a number of independent control loops, corresponding to the number of radiation sources, as in the prior art, in which common control loop the mean radiation power is the measured variable and its error from a nominal value is used as the controlled variable for controlling all of the radiation sources. These radiation sources therefore nominally always have the same electrical power applied to each of them, and this electrical power can be varied over time as appropriate for the control requirement.

The electrical power to be supplied to the radiation sources is thus preferably controlled in such a way that the averaged radiation power remains constant over time.

The control process should be carried out in such a way that the same electrical power, within a predetermined tolerance bandwidth, is supplied to each of the radiation sources. This tolerance bandwidth may, for example, be ±2%.

The radiation powers of the individual radiation sources can be measured at regular time intervals, with the mean radiation power being calculated from this. The control process responds to an incremental reduction in the mean radiation power by uniformly increasing the electrical power to the radiation sources, until the original mean radiation power level is achieved again.

As already stated, the radiation power can be detected by broadband measurement in the range from 300 to 400 nm, corresponding to the IS Standard, using UV sensors designed appropriately for this purpose. As an alternative to this, detection can also be carried out by narrowband measurement, in the range from 330 nm to 350 nm, in accordance with the NB Standard. A further measurement range which is specified in the NB Standard and which can be used for the method according to the invention is that from 410 nm to 430 nm, which is outside the UV, in the visible spectral range.

An arrangement according to the invention for controlling the radiation sources in a weathering apparatus has sensors for measurement of the radiation powers of the radiation sources, and has a monitoring device for calculation of an averaged radiation power from the measured radiation powers and for production of control signals for the electrical power to be supplied to the radiation sources.

The monitoring device has inputs which are connected to the outputs of the sensors, and also has outputs which are connected to control inputs of power supply devices for the radiation sources.

The invention also relates to a weathering apparatus having a weathering chamber, having UV radiation sources and having an arrangement as described above for controlling the radiation sources.

BRIEF DESCRIPTION OF THE DRAWINGS

One exemplary embodiment of an arrangement according to the invention is illustrated schematically in the single drawing FIGURE.

DETAILED DESCRIPTION

A weathering apparatus has a weathering chamber 1 in which material samples to be investigated can be subjected to artificial weathering conditions. For this purpose, a number of UV radiation sources are fitted into openings in an inner wall in the illustrated type of weathering apparatuses. As in the illustrated case, the radiation sources are preferably fitted to one of the two opposite inner walls of the weathering chamber 1 with the largest area. The material samples (not illustrated) to be weathered can be fitted in the opposite inner wall, with these material samples preferably having the normal standard dimensions for this field and being placed in cutouts of appropriate size in this inner wall. These material samples are accordingly arranged opposite the UV radiation sources 2. Each of the UV radiation sources 2 emits a divergent radiation beam. The radiation beams are superimposed on one another on the sample plane. The inner walls of the weathering chamber 1 are preferably provided with a coating that is highly reflective for UV, such as an aluminium coating, in order to make optimum use of the emitted UV radiation. This results in an approximately homogeneous, constant UV radiation power on the sample plane.

The UV radiation sources 2 are formed in particular, but not exclusively, by xenon radiation sources. Their relatively high spectral component in the infrared spectral range is—as mentioned in the introduction—a part of the original problem on which the present invention is based. If desired, an infrared filter can additionally be arranged between the xenon radiation sources and the samples.

However, other radiation sources may also be used, in particular including those in which the initially mentioned problems of unequal infrared radiation load and thus unequal heat application to the samples do not occur, or are not so important. The invention can also advantageously be used with radiation sources such as these to the extent that it solves the problem, which was likewise mentioned in the introduction, of unequal application of electrical power to the radiation sources. By way of example, a halogen lamp, in particular a metal-halogen lamp, may also be used as a radiation source, although it is somewhat more difficult to control radiation sources such as these than xenon lamps. Fluorescent lamps may also be used as radiation sources, although in general these have shorter lives than the radiation sources mentioned above. Furthermore, UV light-emitting diodes may also be used as radiation sources, in particular those based on GaN, in which case the infrared problem would be entirely irrelevant. Recently, it has been possible to use GaN LEDs to satisfactorily cover the entire UV range of the solar spectrum. The achievable radiation densities are already sufficiently high that the radiation power of a conventional xenon lamp can be achieved without any problems by the arrangement of a number of UV LEDs. The radiation sources 2 illustrated in the drawing FIGURE may thus, by way of example, be formed by in each case one individual UV LED or an array of a number of UV LEDs.

Three radiation sources 2 are illustrated in the exemplary embodiment illustrated in the drawing FIGURE. However, this number is irrelevant to the invention. It is also possible to provide two radiation sources, or more than three radiation sources. In addition, these radiation sources need not necessarily be arranged on one and the same inner wall of the weathering chamber. They may also be distributed over different inner walls. In particular, the invention can also be used for different types of weathering apparatuses with a different geometry. The samples to be weathered are either inserted into suitable depressions on the baseplate of the weathering chamber or are inserted in the same way into a holding plate which is arranged above the baseplate, parallel to it, and is mounted in a suitable manner in the weathering chamber.

According to the invention, the radiation power of each of the radiation sources is measured in a predetermined spectral range. In the illustrated exemplary embodiment, UV sensors 4 are used for this purpose, in which case, in principle, one UV sensor 4 is associated with each radiation source 2. These UV sensors 4 are preferably, as illustrated, inserted into openings in a side wall of the weathering chamber 1, in such a way that they are aligned obliquely upwards with respect to the respectively associated radiation source 2. They are preferably designed for a broadband measurement in the UV range from 300 to 400 nm, in accordance with the IS Standard. As an alternative to this, however, they may also be designed in accordance with the NB Standard for narrowband measurements in the range of 340 nm (.+−0.10 nm) or in the already visible region of 420 nm (.+−0.10 nm). However, in the latter case, they would no longer be referred to as UV sensors.

On the output side, the UV sensors 4 are connected to a corresponding number of inputs of a monitoring device 5, to which they supply the measured values of the UV radiation power. The monitoring device 5 calculates the mean value of the radiation powers (as measured by and supplied from the UV sensors 4) of the radiation sources 2, that is to say in particular the arithmetic mean value $$\hat{I}_M = \frac{1}{M} \sum_{N=1}^{M} I_N$$

where M is the number of radiation sources 2, $I_N$ is the radiation power of the N-th radiation source 2, and N is the sequential index of the radiation sources 2.

The monitoring device 5 controls the electrical power to be supplied to the radiation sources 2 on the basis of the mean value of the radiation powers as calculated by it. For this purpose, it is connected to the power supply devices 3 for the radiation sources 2. Each radiation source 2 has its own associated power supply device 3, that is to say a voltage or current source. Each power supply device 3 also has a control input, and each of the control inputs of the power supply devices 3 is connected to a corresponding output of the monitoring device 5.

The control process to be carried out by the monitoring device 5 may, for example, be carried out in such a way that a mean value (which is calculated initially by it during operation of the weathering apparatus) of the radiation power is stored and is then from then regarded as the nominal value for the mean radiation power. The power supply devices 3 are then driven in such a way that the mean radiation power is always maintained at this nominal value, so that it is kept constant for the duration of operation of the weathering apparatus. If the UV radiation power of one or more of the radiation sources 2 thus becomes degraded, the monitoring device 5 thus detects a decrease in the mean radiation power. In response to this, the monitoring device 5 transmits control signals to the power supply devices 3 in such a way that they uniformly increase the electrical power to be supplied to their respective radiation sources 2. By way of example, the monitoring device 5 may be designed such that it uses the decrease in the mean radiation power as determined by it to calculate the amount by which the electrical power supplied by each of the power supply devices 3 must be increased in order to recreate the nominal value of the mean radiation power. The characteristics of the radiation sources 2 may be stored in the monitoring device 5 for this purpose.

It is also possible to provide for the monitoring device 5 to check the radiation powers measured by the UV sensors 4 at regular time intervals, and to use this to calculate an actual value of the mean radiation power. If this actual value differs from the nominal value of the mean radiation power, in particular differing by more than a noise-dependent threshold value, the control process is activated, resulting in the power supply devices 3 increasing or, if appropriate, also reducing, their emitted electrical power.

The control process carried out by the monitoring device 5 may be a simple proportional control process, in which the electrical power is increased in proportion to the magnitude of the decrease in the mean radiation power. However, it is also possible in a manner known per se to provide a more complex control process, for example a proportional integral (PI) control process or a proportional integral differential (PID) control process in particular in order to avoid the oscillations which frequently occur in control processes such as these, in which previously determined values are also taken into account in the determination of the control signal to be supplied to the power supply devices 3, rather than just a currently determined discrepancy between the nominal value and actual value of the mean radiation power.

The invention claimed is:

1. Method for controlling the UV radiation sources in a weathering apparatus, comprising
   providing a plurality of UV radiation sensors each arranged for measuring the radiation power of one of the radiation sources, wherein the number of the UV radiation sensors is the same as the number of the UV radiation sources;
   measuring radiation power of each of the radiation sources in a predetermined spectral range of the radiation emitted from the radiation sources, with the spectral range being chosen such that the measured radiation power is representative of the radiation power in the UV,
   calculating an averaged radiation power from the measured radiation powers by summing the radiation powers of all radiation sources measured by the respective radiation sensors and dividing the sum by the number of the radiation sources, and
   controlling the electrical power to be supplied to the radiation sources in accordance with the averaged radiation power.

2. Method according to claim 1, wherein
   the electrical power is controlled such that the averaged radiation power remains constant over time.

3. Method according to claim 1 or 2, wherein
   the control process is carried out in such a way that the same electrical power, within a predetermined tolerance bandwidth, is supplied to each of the radiation sources.

4. Method according to claim 1 or 2, wherein
   an averaged radiation power is calculated from measured radiation powers at regular time intervals.

5. Arrangement for controlling the UV radiation sources in a weathering apparatus, comprising:
- a plurality of UV radiation sensors for measurement of the radiation powers of the UV radiation sources in a spectral range of the radiation emitted from the radiation sources, wherein the number of the UV radiation sensors is the same as the number of the UV radiation sources, with the spectral range being chosen such that the measured radiation power is representative of the radiation power in the UV,
- a monitoring device for calculating an averaged radiation power from the measured radiation powers by summing the measured radiation powers of all radiation sources and dividing the sum by the number of the radiation source, and for production of control signals for the electrical power to be supplied to the radiation sources.

6. Arrangement according to claim 5, wherein
each radiation source is connected to a power supply device, and each power supply device has a control input which is connected to an output of the monitoring device.

7. Weathering apparatus having a weathering chamber, having UV radiation sources and having an arrangement for controlling the UV radiation sources, according to claim 4.

8. Weathering apparatus according to claim 7, comprising further
- it has a weathering chamber in which the radiation sources and the sensors are accommodated,
- and wherein the radiation sources are arranged along a first wall of the weathering chamber, and the samples to be weathered are arranged along a second wall, which is opposite the first wall, and
- the UV sensors are fitted to a third inner wall, which connects the first wall and the second wall, and in particular are inserted into openings in the third wall.

9. Weathering apparatus according to claim 8, wherein
the samples to be weathered are held by the second wall or a holding plate.

10. Weather apparatus having a weathering chamber having UV radiation sources and having an arrangement for controlling the UV radiation sources according to claim 5.

* * * * *